United States Patent [19]

Herweh

[11] 4,099,910

[45] Jul. 11, 1978

[54] SURFACE MODIFICATION OF POLYMERIC SUBSTRATES VIA INTERACTION WITH AZIDO FORMYL OR AZIDO SULFONYL COMPOUNDS

[75] Inventor: John E. Herweh, Lancaster, Pa.

[73] Assignee: Armstrong Cork Company, Lancaster, Pa.

[21] Appl. No.: 820,050

[22] Filed: Jul. 29, 1977

[51] Int. Cl.² .......................................... D06M 13/38
[52] U.S. Cl. ....................................... 8/115.5; 8/196; 260/349
[58] Field of Search .............. 260/349; 8/115.5, 115.7, 8/196

[56] References Cited

U.S. PATENT DOCUMENTS

| | | | |
|---|---|---|---|
| 2,830,029 | 4/1958 | Adams | 260/349 X |
| 3,298,975 | 1/1967 | Feild et al. | 260/349 X |
| 3,917,656 | 11/1975 | Buckley et al. | 260/349 |

Primary Examiner—John D. Randolph

[57] ABSTRACT

Azido formyl or azido sulfonyl compounds are provided by compounds of the formula $R(CH_2)_mX$ wherein R represents a fluorocarbon or an alkoxy alkyl chain and X represents a sulphonazide or azidoformate group and $m$ is an integer greater than 1. The R group may be $C_2$ to $C_{12}$ linear or branched alkyl, $C_2$ to $C_{12}$ linear or branched alkoxy substituted $C_2$ to $C_{12}$ alkyl, or $C_2$ to $C_{12}$ linear or branched fluoroalkyl. The group $(CH_2)_m$ is $C_2$ to $C_{10}$ linear or branched alkylene. These materials upon thermolysis give rise to a reactive intermediate which adds to and protects polymeric substrates such including polyethylene, polypropylene, polystyrene, the natural rubbers, polyamides, polyesters, polybutadienes, polyisoprenes, butadiene-isoprene copolymer, butyl rubber, ethylene-propylene copolymer, ethylene-propylene-dicyclopentadiene terpolymer, and the like, as well as blends thereof.

11 Claims, No Drawings

SURFACE MODIFICATION OF POLYMERIC SUBSTRATES VIA INTERACTION WITH AZIDO FORMYL OR AZIDO SULFONYL COMPOUNDS

FIELD OF INVENTION

This invention relates to certain novel compounds containing azidoformate or azido sulfonyl groups to the preparation of such compounds and their use as textile surface treating agents, particularly synthetic polymeric textile materials.

THE PRIOR ART

It has become relatively common practice to treat natural and synthetic fibers, yarns, fabrics, and related matter with fire-retardant compounds. While surface application of such fire-retardant materials is notably successful, these coated compounds can be relatively easily removed by washing and/or drycleaning. As such, their durability is quite limited. Further, these surface coatings in many ways affect the quality of the fiber substrates, such generally give textile materials having a more harsh hand or suffering from detracting physical properties, e.g., ease of fiber yellowing, matting of the fibers, etc.

A method to circumvent the problems associated with the application of surface coatings has been the incorporation of fire-retardant materials into the individual polymeric masses. While these do, in fact, add a certain degree of permanency to the fire retardancy of the fibers and textiles, physical characteristics degrade significantly, in some cases to the point making fibers that are totally useless as suitable wearing carpet materials. Further, these additives adversely affect polymer stability and strength.

With the universal recognition of the disadvantages of coatings and incorporation of such fire-retardant materials, the prior art has evolved to the point where active intermediates are caused to react in a chemical manner with fiber surfaces so as to chemically bond with such surfaces. U.S. Pat. No. 3,997,571 discloses the treatment of carpet fibers and the like with fluorocarbon residues containing azido groups, such being used as textile finishing agents. U.S. Pat. No. 3,917,656 similarly discloses azido containing reagents being used to treat textiles and the like. Related art may be found in U.S. Pat. Nos. 3,957,835, 3,814,657 and 3,991,131.

SUMMARY OF THE INVENTION

Thus, according to the present invention, there are provided compounds of the formula $R(CH_2)_mX$ wherein R represents $C_2$ to $C_{12}$ linear or branched fluoroalkyl, $C_2$ to $C_{12}$ linear or branched alkoxy substituted $C_2$ to $C_{12}$ alkyl, and $C_2$ to $C_{12}$ linear or branched alkyl; $(CH_2)_m$ represents a linking group that is $C_2$ to $C_{12}$ linear or branched alkylene; and X represents a sulphonazide or an azidoformate group with m being an integer greater than 1.

DESCRIPTION OF THE PREFERRED EMBODIMENT

The novel azido compounds in accordance with the present invention, particularly the azido formyl compounds, have the general formula $$R(CH_2)_mOC(O)-N_3$$

in which m is 2 to 12 and R is $C_2$ to $C_{12}$ linear or branched fluoroalkyl, $C_2$ to $C_{12}$ linear or branched alkoxy substituted alkyl, or $C_2$ to $C_{12}$ linear or branched alkyl, including the radicals perfluoro-n-propyl, perfluoro-n-pentyl, perfluoro-n-heptyl, perfluoro-n-nonyl, perfluoro decyl, perfluoro isopentyl, perfluoro neopentyl, perfluoro isohepyl, and the like. The carbonyl group may be replaced by the sulfonyl group, thus forming sulfonyl azides of the formula $R(CH_2)_mSO_2N_3$ where R and m are described above.

The compounds in accordance with the present invention have been prepared by the reactions to various substituted or unsubstituted $C_2$ to $C_{12}$ linear or branched aliphatic alcohols in excess phosgene to form the corresponding chloroformates, such followed by reaction of the sodium azide yielding the compounds of the present invention. The general reaction proceeds as follows:

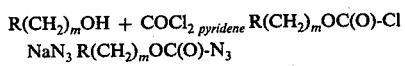

$$R(CH_2)_mOH + COCl_2 \xrightarrow{pyridene} R(CH_2)_mOC(O)\text{-}Cl$$
$$NaN_3 \; R(CH_2)_mOC(O)\text{-}N_3$$

The sulfonyl azides are prepared in a similar manner but using in place of the chloroformate, a sulfonyl chloride.

The above azidoformates (and sulfonyl azides) were used to modify polymeric substrates, particularly synthetic filaments, fibers, yarns, threads, woven, knitted, or otherwise fabricated textile materials or goods made therefrom, whereby the inherent tendency to soil or otherwise accumulate stain may be diminished. Such materials include preferably both polyester and polyamine fibers in the form of ribbon, unbacked carpet, and polypropylene backed carpet.

The surfaces of the textile materials are treated with the compounds of the present invention, and the treated fabrics heated to about 130° – 150° C. to effect a chemical reaction between the polymeric surface and the treating agent. More particularly, in order to carry out the process of the present invention, the following treatment is illustrative:

1. The carpet as received is scoured with trisodiumphosphate followed by a non-ionic surfactant. In some cases, as shown in the illustrative examples, the carpet is first extracted with water in an extractor overnight so as to remove any residual scouring agents and dressings. In other cases, the water extraction was followed by extraction with methanol. All samples subjected to extraction by water or by water followed by methanol were dried in vacuo ($P_2O_5$ present for water extracted samples). The most effective surface treatment is advantageously carried out on surfaces that have been freed from surface contaminants;

2. A chloroform solution of the azido material is applied to the carpet by dipping. Excess solution is allowed to drain from the sample and solvent is then removed by placing the treated samples in a vacuum oven at room temperature and $10^{-2}$ Torr;

3. The treated materials are placed in a preheated oven at 130° – 150° C. for given periods of time. After thermolysis the samples are allowed to cool to room temperature and subsequently washed in chloroform and ether. The solvent washing is conducted so as to remove any reaction products not permanently bonded to the fiber.

The materials treated as outlined above were then separated into the individual fibers and the fibers subjected to the following test procedure in order to illustrate the effectiveness of the surface treatment:

Test #1. The Contact Angle Test, where the change in contact angle of a drop of water on the surface of the untreated and the treated fiber is determined;

Test #2. The 3M Water Resistance Test, such consisting of the implacement of three droplets of 30/70% by volume isopropyl alcohol/water on the carpet samples. If after 10 seconds two or more droplets remained, the sample was rated as passing;

Test #3. The 3M Hydrocarbon Resistance Test AATCC 118-1966T, where drops of standard test liquids are placed on sample surfaces. The repellency rating is based on which of the standard liquids do not wet the carpet surface.

The following two examples illustrate a process for the preparation of the sulfonyl azide and azido formate compounds of use in accordance with the present invention. Although the preparative technique below discloses the synthesis of specific compounds, it can be generally used to prepare compounds of the formula $R(CH_2)_mX$ described earlier.

EXAMPLE 1

4-(Perfluoroisopropoxy)-3,3,4,4-tetrafluorobutylsulfonyl azide

To a stirred aqueous solution (75 ml) of sodium azide (6.5g, 0.08 mol) at r.t. was added in 45 min a solution of the sulfonyl chloride(10) (32.8g, 0.08 mol) in 200 ml of acetone. Upon completing the addition, the turbid reaction was heated to 50° C. and maintained for 4 hrs. The reaction mixture was cooled to r.t. and added to 1 of cold water causing an oil to precipitate. Ethyl ether (400 ml) was added and the two phases were separated, the aqueous phase was extracted consecutively with three 100 ml portions of ether and once with aqueous saturated sodium chloride (150 ml).

After drying over sieves, the filtered ethereal solution was concentrated in vacuo (house vac.) on the Rota-Vap. The residual oil, 32.3g, was distilled at 0.1 mm. The sulfonyl azide 27.9g of a colorless oil(8), b.p. 63°–64°, showed nmr absorptions (CDCl₃) at 3.56 [(m), methylene adjacent to sulfonyl azide] and 2.65 ppm [(m) methylene adjacent to —CF₂-]. Anal. calcd. for $C_7H_4F_{11}N_3O_3S$:C, 20.1; H, 0.96; N, 10.0; S, 7.7; F, 49.9. Found: C, 20.0; H, 0.93; N, 10.2; S, 7.5; F, 49.7.

EXAMPLE 2

1H, 1H, 2H, 2H-Perfluorodecyl azidoformate(12)

1H, 1H, 2H, 2H-perfluorodecyl chloroformate (22.7g, 0.043 mol) dissolved in 90 ml of 1,2-dichloroethane was added to sodium azide (5.6g, 0.086 mol) in 13 ml of water with stirring at r.t. under N₂. Upon completing the addition, the reaction mixture was stirred for 24 hrs. after which the two phase reaction mixture was separated. The organic layer was washed consecutively with 5 ml of water, 5 ml of saturated aqueous and dried over anhydrous magnesium sulfate.

The dried organic phase was filtered and concentrated on the Rota-Vap (house vac., still 50°). The residual oil (28.3g) was subjected to distillation at 0.25 mm, no distillate was obtained at pot temperatures 70°–80°. In order to minimize any decomposition, further attempts to distill the crude azidoformate(12) were discontinued. An infrared spectrum of the crude azidoformate(12) showed azide bands at 2165 & 2125 cm⁻¹ and a strong carbonyl absorption at 1725 cm⁻¹. The nmr spectrum of (12) in CDCl₃ showed absorptions at 4.50 [t,—CH₂-adjacent to —OC(O)N₃] and 2.53 ppm (t,—CH₂-adjacent to —CF₂—). Anal. calcd. for $C_{11}H_4F_{17}N_3O_2$:C, 24.78; H, 0.76; F, 60.58; N, 7.88. Found: C, 24.66; H, 0.61; F,60.67; N, 8.17.

The following table illustrates the results of treatment of nylon carpet backed with polypropylene scrim of the following structure:

Fiber-Allied 6V39 (Type 6) bright yarn, denier 1225 of 70, 18 denier fibers having an assymetric trinodal or 4-cross section. Carpet face weight 10.5 ± 0.25 oz/yd², machine gauge 564, stitch rate 27 per 3 inches and pile height 3/16 inch. The method of treatment is set forth above.

Table

| Example | Azido-Formate | Conc. of Applicator Solv. (% by wt.) | Thermolysis Conditions (Temp., °C./Time, min.) | Contact[a] Angle | 3M Water Resistance | 3M Oil Resistance |
|---|---|---|---|---|---|---|
| Comp. 3 | None | — | 130° /40 | 68 | F[d] | None |
|  | 11 | 2.5 | 130° /40 | 130 (125)[b] 110 (105)[c] | F | — |
| 4 | 12 | 2.5 | 130° /40 | 132 (129) 125 (125) | P | #6 |
| 5 | 12 | 5.0 | 130° /40 | 135 (132) 130 (135) | P | — |
| 6 | 12 | 2.5 | 140° /10 | 128 | P | #5 |
| 7 | 12 | 2.5 | 130° /10 | 118 (128) | F | #1 |
| 8 | 12 | 1.5 | 140° /15 | — | P | #5 |
| Comp. | Zepel[e] | 1.5 | — | — | F | #1 |

[a]Single fiber with water
[b]Average of at least 3 readings on single fiber; figure in ( ) results from second single fiber
[c]Contact angle after 16 hour chloroform extraction in Sohlet
[d]F = fail; P = pass
[e]Trademark, DuPont de Nemoues & Co.

Examples 2 and 3 illustrate a change in surface properties as shown by the high value for contact angle for treated fiber vs. the value for untreated fiber. This high contact angle is an indication of low critical surface energy expected for highly fluorinated materials.

Examples 2, 3, and 4 illustrate the treatment to be permanent. Overnight extraction with CHCl₃ caused only a slight diminution in contact angle.

Example 5 and 6 results directed toward conditions of thermolysis to obtain effective treatment, the higher the temperature, the more effective the treatment.

Examples 7 and 8 comparison of treated sample with Zepel.

In the 3M H₂O resistance test a fail designation does not mean that no treatment was effected. The test has fairly narrow limits, e.g., if contact angle with water is 120° – 125°, sample would fail test. Its use here is, therefore, only relative to the other two tests as establishing that surface treatment had in fact occurred.

As noted from the above table, significant modification of the fiber surface occurs as a result of the application of compounds in accordance with the present invention.

What is claimed is:

1. A compound of the formula $R(CH_2)_mX$ wherein R is $C_2$ to $C_{12}$ linear or branched fluoroalkyl, $C_2$ to $C_{12}$ linear or branched alkoxy substituted $C_2$ to $C_{12}$ alkyl, or $C_2$ to $C_{12}$ linear or branched alkyl; $(CH_2)_m$ represents a linking group that is $C_2$ to $C_{12}$ linear or branched alkylene; and X represents a sulphonazide or azidoformate and m is a whole number greater than 1.

2. A compound perfluoro $C_1$ to $C_{12}$ linear or branched alkoxy-3,3,4,4-tetrafluoro butylsulfonyl azide.

3. The compound of claim 2 wherein said perfluoroalkoxy is the 4-(perfluoroisopropoxy) radical.

4. A compound 1H, 1H, 2H, 2H-perfluoro $C_3$ to $C_{12}$ linear or branched alkyl azidoformate.

5. The compound of claim 4 wherein said perfluoroalkyl is 1H, 1H, 2H, 2H-perfluorodecyl radical.

6. A process for forming an improved textile material comprising
    (a) treating the surface of said textile material with a compound of the formula $R(CH_2)_mX$ wherein R is $C_2$ to $C_{12}$ linear or branched fluoroalkyl, $C_2$ to $C_{12}$ linear or branched alkoxy substituted $C_2$ to $C_{12}$ alkyl, or $C_2$ to $C_{12}$ linear or branched alkyl; $(CH_2)_m$ represents a linking group that is $C_2$ to $C_{12}$ linear or branched alkylene; and X represents a sulphonazide or azidoformate and m is a whole number greater than 1;
    (b) heating said treated textile material to a temperature of 130°–150° C. for a time sufficient to react the second compound with the textile material.

7. The process of claim 6 wherein said compound is perfluoro $C_1$ to $C_{12}$ linear or branched alkoxy-3,3,4,5-tetrafluoro butylsulfonyl azide.

8. The process of claim 7 wherein said perfluoroalkoxy is the 4-(perfluoroisopropoxy) radical.

9. The process of claim 6 wherein said compound is 1H, 1H, 2H, 2H-perfluoro $C_3$ to $C_{12}$ linear or branched alkyl azidoformate.

10. The process of claim 9 wherein said perfluoroalkyl is 1H, 1H, 2H, 2H-perfluorodecyl radical.

11. A woven or knitted textile material produced by the process of claim 6.

* * * * *